United States Patent [19]

Palsgård et al.

[11] Patent Number: 4,946,271
[45] Date of Patent: Aug. 7, 1990

[54] OPTICAL DEVICE

[76] Inventors: Göte Pålsgård, Nygatan 28, 702 11 Örebro; Lars O. Östlin, Gundbo 3328, 822 00 Alfta, both of Sweden

[21] Appl. No.: 153,841
[22] PCT Filed: Jun. 3, 1987
[86] PCT No.: PCT/SE87/00268
   § 371 Date: Jan. 26, 1988
   § 102(e) Date: Jan. 26, 1988
[87] PCT Pub. No.: WO87/07497
   PCT Pub. Date: Dec. 17, 1987

[30] Foreign Application Priority Data

Jun. 4, 1986 [SE] Sweden ................................ 8602521

[51] Int. Cl.⁵ .............................................. A61B 3/14
[52] U.S. Cl. ..................................... 351/210; 351/209
[58] Field of Search ................. 351/209, 210, 41, 158; 250/201

[56] References Cited

U.S. PATENT DOCUMENTS 3,986,030 10/1976 Teltscher ............................ 351/210
4,109,145 8/1978 Graf .
4,568,159 2/1986 Baldwin .............................. 351/210

Primary Examiner—Rodney B. Bovernick
Attorney, Agent, or Firm—Zarley, McKee, Thomte, Voorhees & Sease

[57] ABSTRACT

Disabled persons without capability to speak and to move their arms have great problems to communicate with the environment. A device is intended especially for these persons and comprises means (3-8) adapted to detect the direction of the pupil of one of the eyes of said person and means (9) adapted to evaluate the direction information from said previous means so as to deliver a signal, the character of which depends on the direction of the eye of the person.

6 Claims, 1 Drawing Sheet

OPTICAL DEVICE

THE FIELD OF THE INVENTION AND PRIOR ART

The present invention relates to a device for making it possible for in particular disabled persons without capability to speak and to move their arms to communicate with the environment, but the device of the invention may also have sound and healthy persons as user group.

For disabled persons which have no capability to speak and are nearly totally crippled, in any case not able to point at what they want to have by means of their extremities or by movements thereof tell other what they want, it is desirable to provide a device which makes it possible for these persons to communicate in an easy, reliable and comfortable way with other persons, especially nursing staff, or possibly an apparatus or computer, in order to tell these what kind of wishes they have or else have to tell. Through such a device it would also be possible to control other equipment, such as an apparatus which raises and lowers the pillow or the like.

In order to obtain this it is possible for the nursing staff to either show the disabled person a text and ask him to for instance wink two times if he agrees with the content of the text and once if he has another opinion. It is also possible for the other person to say something to the disabled person and he may answer by appropriate winking.

However, these possibilities presently offered the severely disabled person to communicate with the environment and get his wishes fulfilled are very unsatisfying, since it is necessary that the person is present in order to notice what the disabled person tries to say and the disabled person only is able to answer questions necessitating answers of the yes-and-no-type, if it should be avoided to utilize a very complicated and unreliable winking system.

A completely sound and healthy person having both hands occupied by very difficult employments and desires to control a further machine or the like, but can not remove any of his hands from the employment he is carrying out and has to stay in a very exact position under avoiding great movements, does in the practise find himself in the same situation as the disabled person mentioned above.

This person desires also to control said machine or the like in an easy and reliable way. Such a control carried out by means of a foot pedal may in many situations be unsuitable or not accomplishable, for instance when the person in question carries out the work in the standing position.

SUMMARY OF THE INVENTION

The object of the present invention is to provide a device of the above type which eliminates the drawbacks according to above for the persons with the above-mentioned communication problems.

According to the invention this object is obtained by providing a device of this kind with means adapted to detect the direction of the pupil of one of the eyes of said person and means adapted to evaluate the direction information from said previous means so as to deliver a signal, the character of which depends on the direction of the eye of a person.

Through this it is not required any longer to have a person in the vicinity of a disabled person, in order to enable the latter to express his opinions and wishes, since said means detect in what direction the person is looking and the evaluating means generates a signal which depends on this direction, different directions of the gaze being suitably coordinated with different information which the disabled person wants to communicate to the environment, and the signals from the evaluating means may in this way be decoded in an appropriate manner by a suitable apparatus, for example a computer. The information emanating from the disabled person may control any type of machine, may be stored in a memory of a computer in order to later on be read by nursing staff, be led to a room in which the nursing staff stays in order to, for instance, produce an alarm or the like.

Since it is possible for a person to direct the gaze in many different directions, i.e. towards different objects, the person in question gets a great stock of words or more exactly "stock of opinions" through the device according to the invention. A sound and healthy person having both hands occupied by complicated employments may by means of the device according to the invention get a "third hand" and can through very small body movements control a further machine or the like.

Other preferred features of the device according to the invention will be clearer by the appended description and the dependent claims.

BRIEF DESCRIPTION OF THE DRAWING

With reference to the appended drawing, below follows as specific description of a preferred embodiment of the invention cited as an example.

The drawing shows a very simplified, schematic perspective view of the device according to the invention.

DETAILED DESCRIPTION OF PREFERRED EMBODIMENT OF THE INVENTION

Figure 1:
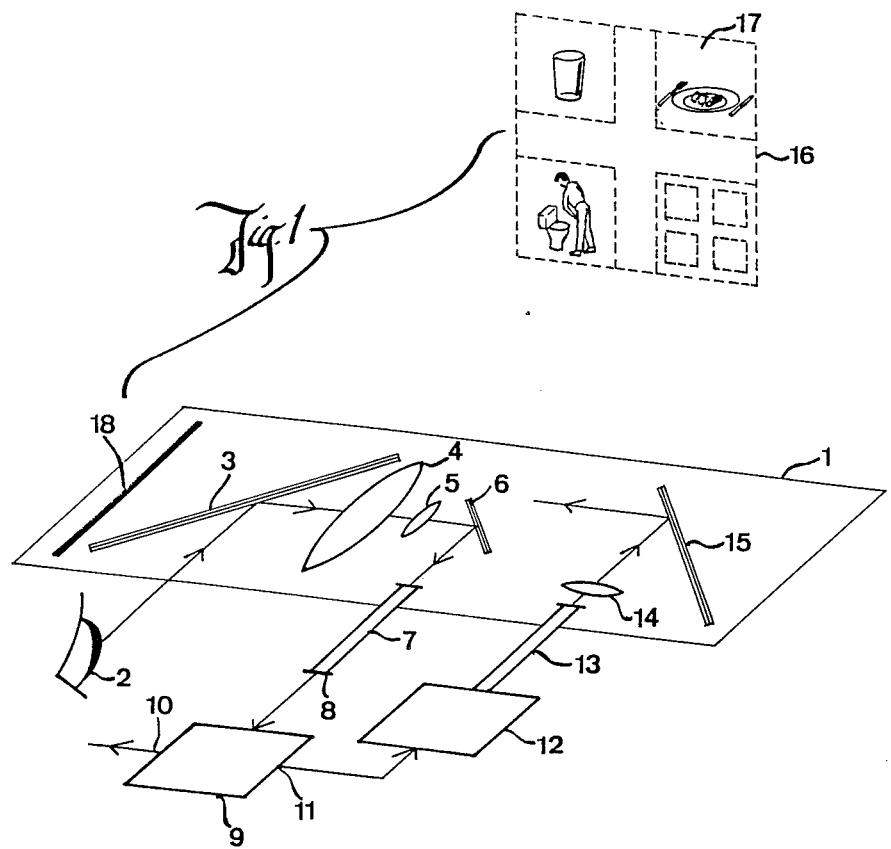

The embodiment of the invention illustrated in the drawing is in particular intended to be used by a disabled person with the communication problems discussed above, and in the following the device according to the invention will be described from this point of view, which however does not at all delimit the invention only to this field of use.

Parts of the device according to the invention are arranged at mutually fixed distances on a common carrier (1), the real configuration of which is not shown in the figure, but which is indicated by a frame 1. The carrier 1 is intended to be located in the vicinity in front of one of the eyes 2 of the person in a fixed and very exact position with respect to the eye. The proportions of the eye 2 of the person and the carrier 1 will in the practise be completely different from the one indicated in the figure, more exactly the carrier should be thinner than illustrated with respect to the eye, but for the sake of illustration the proportions have been changed. Preferably, the carrier 1 is disposed on a spectacle-frame-like element, which for spectacle wearers may be constituted by the spectacles themselves.

The device has a first plane mirror 3 which is so arranged that the light emitted by the eye 2 of the person strikes said mirror and is reflected towards a first lense 4 which is adapted to focus said light, so that it strikes a second, considerably smaller lense 5 which is adapted to influence the light emitted by the eye to strike a comparatively small second plane mirror 6 located there behind, which is so directed that it guides said light towards the cross section surface of a cable 7 with optical fibres. Accordingly, the light struck on said cross section surface corresponds to an image of the eye 2. The light information arriving to the cable 7 is led on by this and transmitted to a light sensitive element 8, for example a photo diod. The light information does here be converted into an image which corresponds to the direction of the eye, which is made possible by the fact that different parts of the eye emit light of different intensity, for instance the light intensity emitted per surface unit from the pupil is considerably lower than the one from the white part of the eye. The mutual location of the elements 3-6, the cross section surface of the cable 7 arranged on the carrier and the eye 2 must of course be very exactly fixed in order to render an accurate determination of the position of the eye possible.

The elements with the reference numbers 3 to 8 form together a means for detecting the direction of the pupil and by that of the eye 2. The cable 7 with the optical fibres may preferably be led to an appropriate place at a distance from the disabled person. The information about the position of the eye is sent on from the light sensitive element 8 to an evaluating means 9, which here is indicated by a block and in the practise can be an appropriate computer unit, which is arranged to evaluate this position information and on different outputs deliver a signal, the character of which depends on the direction of the eye of the person. The output 10 may for example through a lead be connected to an apparatus not shown, which for instance may release an alarm at a certain character of said signal and at other signal characters perform other operations.

The device has also an apparatus 12 preferably located in the vicinity of the evaluating means 9 for showing a disabled person pictures. The showing apparatus 12 is here only indicated by a block and may in the practise be an appropriate picture-generating apparatus, as for example a slide picture projector. The picture shown by the apparatus 12 is through a second cable 13 with optical fibres led to the carrier 1, on which the extremity of said cable 13 is disposed with the cross section surface in the fixed position and so directed that the light from said second cable 13 strikes a third lense 14 located on the carrier, which third lense is adapted to forward the light from the apparatus 12 towards a third plane mirror 15, which is so arranged that it reflects the latter light towards the first lense 4, but beside the second plane mirror 6 and the second lense 5. The light from the apparatus 12 will strike the first plane mirror 3 and behind this plane mirror produce a virtual image 16 perceptable to the eye 2, which picture corresponds to the picture generated by the showing apparatus 12.

The picture 16 shown to the disabled person has preferably the form of a "menu", which in the example has been represented by means of four different picture fields 17. In the example the different picture fields represent the questions if the person desires to drink something, eat something, carry out his toilet or get a new picture shown by the apparatus 12. Preferably, the different picture fields 17 are located at a certain distance from each other, so as to force the eye 2 of the person to carry out a direction change which can be registered with reliability when it moves again from one picture field to another.

In order to reduce the demand for accurate adjustement of a carrier 1 with respect to the eye 2 of the person, the person may in every opportunity of communication with the device first of all look at differently located signs on a first picture, whereupon a computer connected thereto may define a system of coordinates. After that it is only necessary to assure a fixed mutual location during the continued communication, or possibly check the system of coordinates after a certain number of pictures and if necessary define it again.

Preferably, light emitting diodes are provided, which shine in the square in question as a confirmation of the release of the desired function by the device. Preferably, these pictures are also shown by the apparatus 12.

The first plane mirror 3 is preferably semi-transparent, especially in order to make it possible for the person to see the surroundings, but also so as to make it possible for light from the surroundings to penetrate the mirror and strike the eye 2 of the person, so that it is partly reflected by the latter and generates an image of the instantaneous position of the eye. In order to prevent such environment light from incide upon the second plane mirror 6 and be reflected towards the cable 7, resulting in incorrect information about the position of the eye 2 a black plate 18 is arranged on the carrier 1 in an appropriate position with respect to the optical system constituted by the elements 3-7.

The evaluating means 9 is through the output 11 also connected to the showing apparatus 12 in order to render a control of the picture showing carried out by means of the position of the eye 2 possible.

The function of the device according to the invention is as follows: By means of the showing apparatus 12 and the optical system with the elements 13, 14, 15, 4 and 3 a virtual image 16 perceptable by the eye 2 of the person is shown. The person directs the gaze towards the picture field 17 corresponding to his wish. An image of the eye 2 which corresponds to this gaze direction is led through the optical system 3, 4, 5, 6, 7 to the light sensitive element 8 and then to the evaluating means 9. The evaluating means is adapted to, when the gaze of the person has rested a predetermined period of time, the length of which preferably is adjustable according to the ability and the wishes of the user, upon a picture field forward appropriate information through one of the outputs 10 and 11. This is done in order to without doubt eliminate possible incorrect conclusions of what the person really wants. The information from the evaluating means brings an apparatus not shown to carry out certain operations or control the showing apparatus 12, for instance when the person in question rests the gaze of his eyes on the lower, right picture field for a change of picture.

Preferably, the showing apparatus 12 is intended to normally be switched off at the same time as the detecting means 3-8 is adapted to permanently detect the direction of the eye and the evaluating means is arranged to, if the person during the certain period of time direct the gaze in a direction he otherwise seldom or never look in for a longer period of time, through the output 11 send a signal to the apparatus 12 for switching it on in order to show pictures. This characteristic of the device according to the invention makes it possible for the disabled person to be spared from looking on pictures during periods of time when he does not desire to send any messages. Preferably, for this reason the device is also so designed that it through the evaluating means 9, when the apparatus 12 is switched on, automatically switches said apparatus off in the case that the gaze of the eye of the person during a predetermined period of time does not rest on any of the picture fields 17. To this end the person can during a predetermined period of time, for example five seconds, rest the gaze on the middle of the picture.

The invention is of course not delimited to the prefered embodiment described above, but several modification possibilities thereof would be apparent to a man skilled in the art without diverting from the spirit of the invention.

When the device according to the invention is applied to a sound and healthy person which has both hands occupied according to above, the output 10 of the evaluating means 9 may be led to an appropriate machine or the like for controlling the same.

It is also conceivable that the optical cable 7 is left out and the light sensitive element 8 is located on the carrier 1, so that the eye image from the second plane mirror 6 strikes directly upon the light sensitive element 8.

The whole device could also be arranged on a carrier 1. This carrier could also be designed in unnumerable varying ways.

The elements arranged for showing pictures, the apparatus 12, the cable 13, the lense 14 and the mirror 15 could for instance be exchanged for a slide picture projector located at a fixed distance from a person, and the first plane mirror 3 would not any longer have anything to do with this picture showing. However, this procedure could be less suitable, since it requires a fixed position of the head of the person.

We claim:

1. A device for allowing persons without the capability to speak and to move their arms to communicate with the environment, comprising:

detection means for detecting the direction of the pupil of one of the eyes of said person;

evaluation means for evaluating the direction information from said detection means so as to deliver a signal corresponding to the direction of the eye of the person;

an apparatus arranged to show one or more pictures to the person, said pictures being divided into a number of fields with symbols or text corresponding to different information, which the person may be expected to wish to communicate to another person or a machine;

said detection means being arranged to detect towards which field of said picture the person directs his gaze;

the detection means including a light sensitive element towards which the light emitted by one eye of the person is intended to directly or indirectly fall, and that said element is adapted to at different portions thereof deliver a signal corresponding to the intensity of the incident light so as to be able to give the evaluation means information making it possible to determine the direction of the eye; and the detection means also including an optical system having a first set of mirrors and a first set of lenses which are arranged to throw an image of the eye of the person directly upon said light sensitive element.

2. A device according to claim 1 wherein the first set of mirrors includes a first plane mirror located in a predetermined position in front of the eye of said person, and said device further comprising a second optical system including a second mirror and lens set arranged with said first plane mirror to create an image shown by the apparatus behind the first plane mirror.

3. A device according to claim 2 further comprising a carrier for carrying a picture emitting element of the apparatus and for carrying the optical system of the detection means at mutually fixed distances, and the carrier being located adjacent to the eyes of said person and in a predetermined position with respect to the eye to be examined.

4. A device according to claim 3, characterized in that said first plane mirror is semi-transparent so as to enable the eye of said person to be struck by environment light which then can be reflected by the eye to the detection means and so as to enable the person to see the surrounding.

5. A device according to claim 1, characterized in that the evaluation means is arranged to, when the gaze of the person has rested upon a picture field for a predetermined period of time, send the signal to an appropriate receiver.

6. A device according to claim 1, characterized in that the apparatus is intended to normally be switched off and the detection means is arranged to constantly detect the direction of the eye and that the evaluation means is arranged to, when the person directs the gaze in a predetermined direction, send a signal to the apparatus for switching it on in order to show pictures.

* * * * *